United States Patent [19]

Aburaki et al.

[11] Patent Number: 4,659,812
[45] Date of Patent: Apr. 21, 1987

[54] CEPHALOSPORIN INTERMEDIATES

[75] Inventors: Shimpei Aburaki, Tokyo; Yukio Narita; Jun Okumura, both of Yokohama; Takayuki Naito, Kawasaki, all of Japan; Donald G. Walker, Liverpool, N.Y.

[73] Assignee: Bristol-Myers Company, New York, N.Y.

[21] Appl. No.: 767,562

[22] Filed: Aug. 20, 1985

[51] Int. Cl.$^4$ ........................................... C07D 501/18
[52] U.S. Cl. .................................................. 540/222
[58] Field of Search ...................... 544/22, 16; 540/22, 540/215

[56] References Cited

U.S. PATENT DOCUMENTS

| | | | |
|---|---|---|---|
| 4,168,309 | 9/1979 | Ayres | 424/246 |
| 4,406,899 | 2/1983 | Aburaki et al. | 424/246 |
| 4,423,213 | 12/1983 | Takaya et al. | 544/16 |

FOREIGN PATENT DOCUMENTS 3,419,012  11/1985  Fed. Rep. of Germany .

*Primary Examiner*—Donald G. Daus
*Assistant Examiner*—Barbara Cassatt
*Attorney, Agent, or Firm*—Aldo A. Algieri

[57] ABSTRACT

Temperature stable crystalline mono-hydrochloric and sulfuric acid addition salts of 7-amino-3-(1-methylpyrrolidinio)methyl-3-cephem-4-carboxylate substantially free of $\Delta^2$ isomer are intermediates for the preparation of broad spectrum 7-[$\alpha$-(2-aminothiazol-4-yl)-$\alpha$-(Z)-methoxyiminoacetamido]-3-[(1-methyl-1-pyrrolidinio)-methyl]-3-cephem-4-carboxylates. The monohydrochloric acid addition salt intermediate is prepared by a process comprising the steps of (1) neutralizing diphenylmethyl 7-amino-3-chloromethyl-3-cephem-4-carboxylate hydrochloride, (2) reacting the resulting free base with benzaldehyde to produce diphenylmethyl 7-benzylideneamino-3-chloromethyl-3-cephem-4-carboxylate, (3) reacting the resulting product with sodium iodide to convert the chloromethyl group to iodomethyl, (4) reacting the resulting product with N-methylpyrrolidine to give the quaternized product diphenylmethyl 7-benzylideneamino-3-(1-methylpyrrolidinio)methyl-3-cephem-4-carboxylate iodide, and (5) reacting with hydrochloric acid to form said intermediate.

3 Claims, No Drawings

CEPHALOSPORIN INTERMEDIATES

TECHNICAL FIELD

This invention is directed to the temperature stable salts of a cephalosporin intermediate, which are substantially free of $\Delta^2$ isomer and which are convertible into broad spectrum cephalosporin antibiotics without a carboxyl group deblocking step. This invention is also directed to a method for making these salts.

BACKGROUND AND DESCRIPTION OF THE PRIOR ART

U.S. Pat. No. 4,406,899, issued Sept. 27, 1983 to Aburaki et al., discloses compounds of the formulae

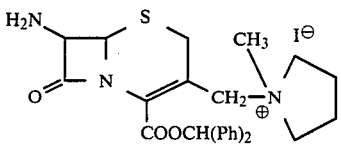

wherein Ph is phenyl, and

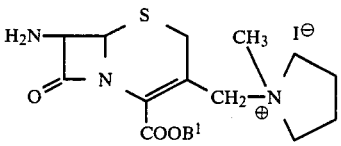

or an N-silyl derivative thereof, wherein $B^1$ is hydrogen or a conventional carboxyl-protecting group. These compounds are not exemplified in the patent, but are disclosed by structural formulae only, as intermediates in an alternate reaction scheme for the preparation of certain cephalosporins (by acylation and then deblocking of the protected carboxyl group). The reaction scheme actually exemplified did not utilize these compounds (and also required deblocking of the protected carboxyl group as the final step). Each of the final products of U.S. Pat. No. 4,406,899 required a chromatographic purification step to separate the mixture of $\Delta^2$ and $\Delta^3$ isomers which were produced.

U.S. Pat. No. 4,168,309, issued Sept. 18, 1979 to Barry E. Ayres, discloses compounds of the formula

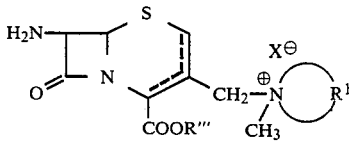

wherein $R'''$ is a carboxyl-protecting group; $R^1$, taken together with the carbon atom to which it is attached, forms an optionally substituted saturated or partially saturated 4–10 membered heterocyclic ring which may contain one or more further heteroatoms selected from O, N and S; the dotted line indicating a ceph-2-em or a ceph-3-em compound; and $X^\ominus$ representing an anion; and acid addition salts or an N-silylated derivative thereof.

These compounds are not exemplified but are disclosed by structural formula only as intermediates in an alternative synthesis of certain cephalosporins (by acylation and then deblocking of the protected carboxyl group). The reaction scheme actually exemplified did not utilize these compounds (and also required deblocking of the protected carboxyl group as a final step).

The use of blocked carboxyl groups in the processes of the above two patents has the disadvantage of requiring deblocking after acylating whereby acyl group is lost in the deblocking step due to less than 100% yield in the deblocking step.

SUMMARY OF THE INVENTION

Novel intermediates have been discovered herein which do not require carboxyl group deblocking on conversion to N-acylated compounds and thus offer an efficiency in acylating agent use. The intermediates herein have the additional advantage of being temperature stable so that they can be stored and converted to the end product when desired. An important advantage of this invention is to afford the intermediate (VI), and subsequently the desired final cephalosporin, substantially free of $\Delta^2$ isomer, without the need for chromatographic purification.

The compounds herein are temperature stable crystalline salts of 7-amino-3-(1-methylpyrrolidinio)methyl-3-cephem-4-carboxylate substantially free of $\Delta^2$ isomer, selected from the group consisting of the mono-hydrochloric and sulfuric acid addition salts. As a result of being free of $\Delta^2$ isomer, they are convertible to acylated products substantially free of $\Delta^2$ isomer which are useful as injectible antibiotics. The compounds herein are readily converted into broad spectrum antibiotic cephalosporins by acylating with 1-benzotriazolyl(Z)-2-(2-aminothiazol-4-yl)-2-methoxyiminoacetate active ester, and deblocking of the 4-carboxylate group is not necessary since it is not blocked.

The mono-hydrochloric acid addition salt is prepared by a process comprising the steps of:

(a) reacting diphenylmethyl 7-amino-3-chloromethyl-3-cephem-4-carboxylate (free base form) with benzaldehyde to form the Schiff's base, i.e. diphenylmethyl 7-benzylideneamino-3-chloromethyl-3-cephem-4-carboxylate, (b) iodinating the Schiff's base product of step (a) by reacting it with sodium iodide, thereby producing 7-benzylideneamino-3-iodomethyl-3-cephem-4-carboxylate, (c) quaternizing the product of step (b) by reacting it with N-methylpyrrolidine, thereby producing diphenylmethyl 7-benzylideneamino-3-(1-methylpyrrolidinio)methyl-3-cephem-4-carboxylate iodide, and (d) deblocking and forming the mono-hydrochloric acid addition salt by admixing hydrochloric acid, formic acid, and the product of step (c), reacting for a time ranging from about 30 minutes to about 5 hours, and recovering crystalline product substantially free of $\Delta^2$ isomer.

The sulfuric acid addition salt is prepared by the process described above, but using sulfuric acid in place of hydrochloric acid in step (d).

DETAILED DESCRIPTION

The compounds herein have the structural formula set forth below

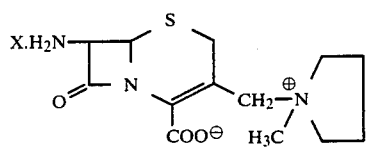

wherein X is HCl or H₂SO₄.

The mono-hydrochloric acid addition salt herein, i.e. the compound of the above structural formula where X is HCl, is preferably made by a process wherein the product of step (b) referred to above is not isolated but rather the reaction mixture resulting from step (b) is used in step (c) referred to above; this is because the product of step (b), i.e. 7-benzylideneamino-3-iodomethyl-3-cephem-4-carboxylate is not very stable. It is also possible to carry out the preparation by carrying out steps (a)–(c) without isolating the products of steps (a) and (b) and/or to prepare the diphenylmethyl 7-amino-3-chloromethyl-3-cephem-4-carboxylate (free base form) and to use the resulting reaction mixture in step (a) without isolation of the free base form.

The diphenylmethyl (sometimes referred to as benzhydryl) 7-amino-3-chloromethyl-3-cephem-4-carboxylate reactant for step (a) is prepared as described in Preparation No. 4 at Column 13 of Aburaki et al. U.S. Pat. No. 4,406,899. It is also readily prepared by neutralizing, e.g. with NaOH or NaHCO₃, the hydrochloride salt, the preparation of which is described in Example III. The reaction equation for the neutralization is set forth below wherein DPM stands for diphenylmethyl.

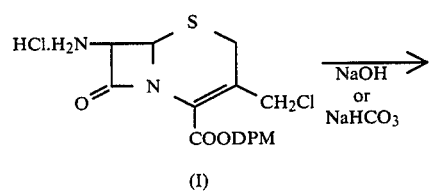

The reaction equations for the various steps in forming the mono-hydrochloric or sulfuric acid addition salt herein are set forth below.

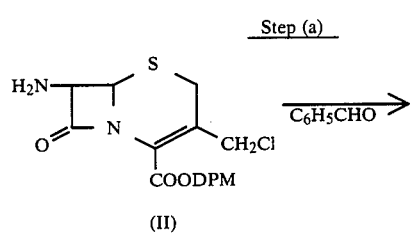

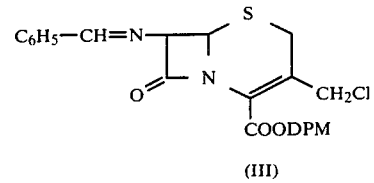

Step (b)

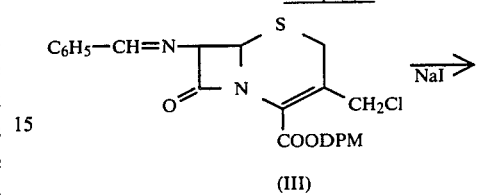

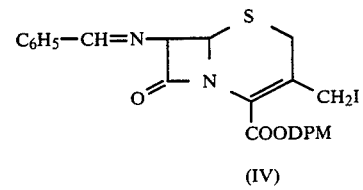

Step (c)

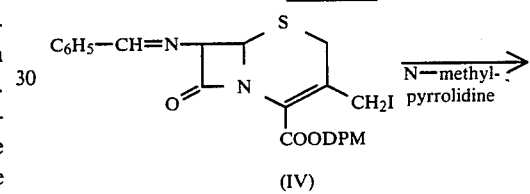

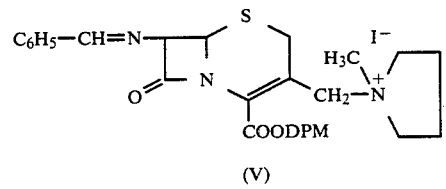

Step (d)

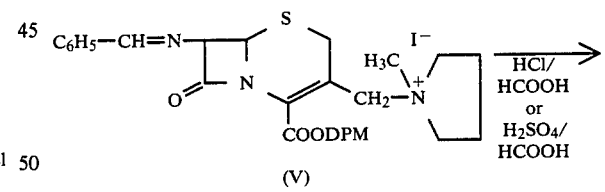

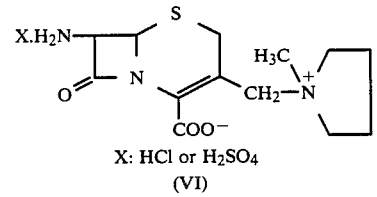

X: HCl or H₂SO₄
(VI)

We turn now to the various reactions in more detail.

The neutralization of the hydrochloride (I) to form the free base starting material (II) is readily carried out over a time period ranging from about 5 minutes to about 1 hour, e.g. using aqueous sodium hydroxide in an organic solvent such as methylene chloride or ethyl acetate solvent at 0°–5° C. (an ice water bath) or using NaHCO₃ in an organic solvent such as methylene chloride or ethyl acetate at room temperature. Neutralization with NaHCO3 has the disadvantage of CO2 evolving.

ing the compounds herein with 1-benzotriazolyl(Z)-2-(2-aminothiazol-4-yl)-2-methoxyiminoacetate active ester. The reaction equation is set forth below.

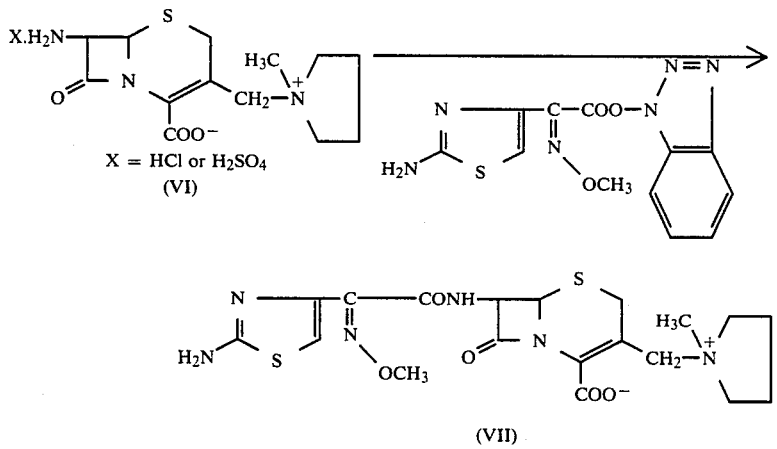

Turning now to step (a), this reaction is readily carried out in the presence of a dehydrating agent, such as molecular sieves, magnesium sulfate or sodium sulfate in an organic solvent such as methylene chloride or ethyl acetate at room temperature over a period ranging from about 30 minutes to about 5 hours. At least one equivalent of benzaldehyde is used, preferably from about 1.1 to about 1.3 equivalents.

Turning now to step (b), this reaction is readily carried out with the starting material (III) dissolved in an organic solvent such as acetone or ethyl acetate or carbon tetrachloride or toluene and the sodium iodide in solution in acetone at room temperature over a period ranging from about 15 minutes to about 5 hours. As indicated above, the reaction product (IV) is not very stable, so it is preferred not to isolate it but rather to utilize the resulting reaction mixture in step (c). At least one equivalent of sodium iodide is used, preferably from about 1.1 to about 1.3 equivalents.

Turning now to step (c), this step is readily carried out in carbon tetrachloride or toluene at $-10°$ C. to $5°$ C. for 15 minutes to two hours. If the reaction mixture from step (b) is utilized without isolating starting material (IV), the reaction mixture from step (b) is preferably simply diluted with carbon tetrachloride or toluene without intermediate concentration. At least one equivalent of N-methylpyrrolidine is used, preferably from about 1.1 to about 1.3 equivalents.

Turning now to step (d) herein, this is readily carried out by adding concentrated HCl to (V) dissolved in an organic acid such as acetic acid or formic acid or by adding (V) to an admixture of hydrochloric acid and formic acid and reacting at room temperature for about 30 minutes to about 5 hours, preferably for from about 45 minutes to about 2 hours.

The use of sulfuric acid in step (d) instead of hydrochloric acid affords the sulfate of Compound (VI) (X=H2SO4).

Both products (VI) (X=HCl and H2SO4) can be easily crystallized out of the reaction mixture, substantially free of $\Delta^2$ isomer, without using any chromatographic purification.

The compounds herein are readily converted to 7-[α-(2-aminothiazol-4-yl)-α-(Z)-methoxyiminoacetamido]-3-[(1-methyl-1-pyrrolidinio)methyl]-3-cephem-4-carboxylate broad spectrum antibiotics (VII) by N-acylating the compounds herein with 1-benzotriazolyl(Z)-2-(2-aminothiazol-4-yl)-2-methoxyiminoacetate active ester. The reaction equation is set forth below.

This reaction is readily carried out in the presence of N,N-dimethylaniline in dimethylformamide at room temperature over a period of 10-20 hours; or by dissolving (VI) in water and dimethylformamide and adding sodium bicarbonate with ice cooling and reacting at room temperature for about 30 minutes to about 5 hours; or by dissolving (VI) in water, cooling to 5°-15° C., adding NaOH dropwise to pH 5.5-6, adding tetrahydrofuran, adding sodium hydroxide to adjust the pH to 6.7-6.9, adding the active ester reactant and reacting for 1 to 5 hours at room temperature. The active ester is a known compound and is described in Hoechst, Japan Kokai No. 54-95593 (7/28/79) and German Application No. 2758000.3 (12/24/77). The utility of the compounds (VII) is shown in Aburaki et al., U.S. Pat. No. 4,406,899.

The following specific examples illustrate the invention.

EXAMPLE I

Preparation of (VI) With Isolation of (III), (V) and (VI)

(A) Preparation of (III) From (I)

To a stirred suspension of diphenylmethyl 7-amino-3-chloromethyl-3-cephem-4-carboxylate hydrochloric (I) (50 g, 0.11 mole) in ethyl acetate (400 ml) and water (150 ml) was added 1N NaOH (200 ml) under cooling on an ice water bath. Stirring was continued for 30 minutes to give a clear two-phase solution. The ethyl acetate layer was separated, washed with water (300 ml) and dried over anhydrous Na2SO4 (100 g). The ethyl acetate solution (without removing Na2SO4) was mixed with benzaldehyde (14.2 g, 0.13 mole) and the mixture was stirred for 2 hours at room temperature. The insoluble material (Na2SO4) was filtered off. The filtrate was concentrated under reduced pressure. To the concentrate (200 ml) was added n-heptane (400 ml) to precipitate 47.6 g (86%) of the crystalline product (III), which was collected by filtration. The filtrate was concentrated to about 100 ml and treated with n-heptane (300 ml) to give 4.6 g (8%) of the second crop. Total yield of (III) was 52.2 g (94%). Estimated purity 95% (by HPLC). Mp. 110°-111° C. Pale yellow prisms.

IR: $\nu_{max}^{KBr}$ cm$^{-1}$ 1780, 1730, 1635.

UV: $\lambda_{max}^{EtOH}$ nm($\epsilon$) 215 (27600), 258 (25500).

PMR: $\delta^{CDCl_3}$ ppm 3.40 and 3.70 (2H, ABq, J=18 Hz, H-2), 4.28 and 4.47 (2H, ABq, J=12 Hz, CH2—Cl), 5.18

(1H, d, J=4.5 Hz, H-6), 5.43 (1H, dd, J=4.5 and 1.5 Hz, H-7), 6.98 (1H, s, CHPh$_2$), 7.0-7.6 (15H, m, Ph), 8.59 (1H, d, J=1.5 Hz, $\overline{\text{Ph—CH}}$=N—).

Anal. Calc'd. for C$_{28}$H$_{23}$N$_2$SCl: C, 66.86; H, 4.61; N, 5.57; S, 6.37; Cl, 7.05%. Found: C, 66.82; H, 4.78; N, 5.80; S, 6.39; Cl, 6.60%.

(B) Preparation of (V) From (III)

To a solution of (III), 52 g, 0.103 mole, in carbon tetrachloride (1 L) was added dropwise a solution of sodium iodide (18.6 g, 0.12 mole) in acetone (200 ml) under stirring. After the addition was completed, the mixture was stirred for 40 minutes at room temperature and filtered through a diatomaceous earth pad. The filtrate was washed consecutively with saturated solutions of Na$_2$S$_2$O$_3$ (750 ml) and NaCl (700 ml×2), dried over anhydrous Na$_2$SO$_4$ (100 g) and filtered. To the chilled (0° C.) and stirred filtrate was added dropwise over a period of 30 minutes a solution of N-methylpyrrolidine (11.8 ml, 0.11 mole) in carbon tetrachloride (50 ml). The mixture was stirred for additional one hour at 0°-5° C. to afford a precipitate, which was collected by filtration, washed with carbon tetrachloride (300 ml) and dried over P$_2$O$_5$ in vacuo to give 70 g of Compound (V). Estimated purity 60%. Mp. 120° C. (dec.). Yield 60% from (III), based on estimated purity of (V).

PMR: $\delta^{CDCl_3}$ ppm ca. 2.0 (4H, m, C—CH$_2$ of pyrrolidine), 2.78 (3H, s, N—Me$^+$), ca. 3.3 (2H, m, H-2), ca. 3.6 (4H, m, N—CH$_2$ of pyrrolidine), 5.37 (1H, d, J=5.0 Hz, H-6), 5.75 (1H, d, J=5.0 Hz, H-7), 6.96 (1H, s, CH—Ph$_2$), 7.3-7.9 (15H, m, Ph), ca. 8.5 (1H, br-s, $\overline{\text{PhCH}}$=N—).

(C) Preparation of (VI, X=HCl) From (V)

A mixture of (V), (68 g, 60% pure), 98% formic acid (68 ml) and concentrated HCl (42 ml) was stirred at room temperature for 1 hour and then poured into acetone (2.5 L) under vigorous stirring. The precipitate which formed was collected by filtration and dried to give a hygroscopic solid (30 g), which was dissolved in water (300 ml), decolorized, and then crystallized by adding acetone (1.5 L) and then chilling to about 0° C., to afford 13.7 g of Compound (VI) as colorless prisms. Mp. 165° C. (dec.). Estimated purity >95% (by HPLC and PMR). Yield 62%, calculated based on estimated purity of (V).

IR: $\nu_{max}^{KBr}$ cm$^{-1}$ 3400, 1800, 1595.

UV: $\lambda_{max}^{Phosphate\ buffer\ (pH\ 7)}$ nm($\epsilon$) 267 (9000).

PMR: $\delta^{D_2O}$ ppm 2.30 (4H, m, C—CH$_2$ of pyrrolidine), 3.09 (3H, s, N—Me$^\oplus$), ca. 3.6 (4H, m, N—CH$_2$ of pyrrolidine), 3.62 and 4.07 (2H, ABq, J=18 Hz, H-2), 4.08 and 4.80 (2H, ABq, J=14 Hz, CH$_2$—N$^\oplus$), 5.27 (1H, d, J=5 Hz, H-6), 5.48 (1H, d, H-7).

Anal. Calc'd. for C$_{13}$H$_{19}$N$_3$O$_3$SHCl$_2$H$_2$O: C, 42.22; H, 6.54; N, 11.36; S, 8.67; Cl, 9.59%. Found: C, 42.24; H, 6.24; N, 11.33; S, 8.91; Cl, 10.22%.

(D) Preparation of (VI, X=H$_2$SO$_4$) From (V)

To a stirred solution of (V), (9.0 g, 13.3 mmole) in formic acid (98%, 9 ml) was added 2M sulfuric acid (6.63 ml), and the mixture was stirred for 1 hour at room temperature. The reaction mixture was poured into acetone (400 ml), and the resulting precipitate was collected by filtration to give a crude product (3.0 g). Recrystallization of the crude powder from aqueous acetone (1:5, 90 ml) afforded the compound (VI) (X=H$_2$SO$_4$) (745 mg, 14%) as colorless plates. Mp. 135° C. (dec.).

NMR: $\delta$(D$_2$O) in ppm 2.38 (4H, m), 3.15 (3H, s), 5.34 (1H, d, J=4.5 Hz), 5.06 (1H, d, J=4.5 Hz).

Anal. Calc'd for C$_{13}$H$_{19}$N$_3$O$_3$S.H$_2$SO$_4$: C, 39.48; H, 5.34; N, 10.63; S, 16.22%. Found: C, 40.34; H, 5.55; N, 10.64; S, 14.97%.

EXAMPLE II

Preparation of (V) Starting With (I) Without Isolation of Intermediates

A suspension of Compound (I), 50 g, 110 mmoles, in ethyl acetate (500 ml) was shaken with a saturated NaHCO$_3$ solution (500 ml) at room temperature for 5 minutes to give a clear two-phase solution. The organic phase was separated, washed with a saturated NaCl solution (100 ml) and dried over anhydrous Na$_2$SO$_4$ (100 g). To the ethyl acetate solution (containing Na$_2$SO$_4$) was added benzaldehyde (12 ml, 120 mmoles), and the mixture was stirred at room temperature for 1.5 hours, mixed with a solution of sodium iodide (20 g, 130 mmoles) in acetone (100 ml) and then stirred in the dark for additional 1 hour. The mixture was filtered through a layer of diatomaceous earth. The filtrate was washed successively with saturated solutions of Na$_2$S$_2$O$_3$ and NaCl, dried over anhydrous Na$_2$SO$_4$ and evaporated below 30° C. under diminished pressure.

The resulting syrup containing the iodo compound (IV) was diluted with carbon tetrachloride (1.3 L), and the insolubles were removed by filtration. To the filtrate was added dropwise N-methylpyrrolidine (13 ml, 120 mmoles), and the mixture was vigorously stirred at 0° C. for 1 hour. The precipitate which formed was collected by filtration and dried to afford 68 g of the quaternized Compound (V). Estimated purity 60% (by HPLC). Yield 54% from (I), calculated based on estimated purity of (V).

The Compound (V) is readily converted to Compound (VI) as in Example I.

EXAMPLE III

Preparation of (VI, X=HCl) With Isolation of (II), (III), (IV), (V) and (VI, X=HCl)

A suspension of diphenylmethyl 7-amino-3-chloromethyl-3-cephem-4-carboxylate hydrochloride (I) (50 g) in ethyl acetate (500 ml) was shaken with a saturated aqueous solution of sodium bicarbonate (500 ml) for 5 minutes to give a clear two-phase solution. The organic phase was separated, washed with a saturated NaCl solution, dried over Na$_2$SO$_4$ and concentrated under reduced pressure in a rotary evaporator. The concentrate (ca. 50 ml) was poured into n-heptane (500 ml) to afford a semicrystalline precipitate of (II) (44.8 g; yield 97.5%). 95% pure [HPLC; Lichrosorb RP-18 (4×300 mm); 80% acetonitrile/water; 1.5 ml/minute; hereinafter System A; Retention Time 3.5 minutes]. Mp. 150° C. (dec.).

PMR: $\delta^{CDCl_3}$ ppm ca. 3.5 (br s, 2H, H-2), ca. 4.3 (br s, 2H, CH$_2$—Cl), 6.95 (s, 1H, CHPh$_2$) and ca. 7.3 (m, 10H, Ph).

A mixture of (II) (5.0 g, 12 mmoles), benzaldehyde (1.3 ml, 13 mmoles) and sodium sulfate (5.0 g) in ethyl acetate (50 ml) was stirred at room temperature for 2 hours (a clear solution was obtained within 30 minutes). The solution was evaporated, the residual syrup was agitated in n-heptane (50 ml) and the supernatant was removed by decantation. The residue was evaporated to dryness to afford the Compound (III) as amorphous solid (5.6 g; 92%). 80% pure (HPLC: System A, RT 6.0 minutes). A part of this sample was recrystallized from ether and hexane to afford colorless plates of (III). >95% pure (by HPLC). Mp. 110°-111° C.

IR: $\nu_{max}^{KBr}$ cm$^{-1}$ 1780, 1730, 1635.

UV: $\lambda_{max}^{MeOH}$ nm($\epsilon$) 258 (25000).

PMR: $\delta^{CDCl_3}$ ppm 3.40 and 3.70 (2H, ABq, J=18 Hz, H-2), 4.28 and 4.47 (2H, ABq, J=12 Hz, CH$_2$—Cl), 5.18 (1H, d, J$_{6,7}$=4.5 Hz, H-6), 5.43 (1H, dd, J$_{7, CH=N-}$=1.5 Hz, H-7), 6.98 (1H, s, CHPh$_2$), ca. 7.3 and 7.7 (15H, m, Ph) and 8.59 (1H, d, Ph—CH=N—).

To a solution of (III) (3.3 g, 6.6 mmoles) in ethyl acetate (33 ml) was added a solution of sodium iodide (1.48 g, 9.9 mmoles) in acetone (6.6 ml), and the mixture was stirred at room temperature for 1 hour. The reaction mixture was washed with water (10 ml), a saturated Na$_2$S$_2$O$_3$ solution (10 ml) and a saturated NaCl solution (10 ml), successively, and then dried and evaporated to dryness to afford the Compound (IV) (3.8 g, 97.5%), which was unstable to decompose when kept at room temperature for several days. 65% pure (HPLC: System A, RT 7.0 minutes).

PMR: $\delta^{CDCl_3}$ ppm 3.37 and 3.81 (2H, ABq, J=18 Hz, H-2), 4.17 and 4.40 (2H, ABq, J=10 Hz, CH$_2$—I), 5.07 (1H, d, J$_{6,7}$=5.0 Hz, H-6), 5.30 (1H, dd, J$_{7, CH=N-}$=1.5 Hz, H-7), 6.97 (1H, s, CHPh$_2$), ca. 7.3 and 7.7 (15H, m, Ph) and 8.52 (1H, d, Ph—CH=N—).

A mixture of (IV) (2.91 g, 4.90 mmoles) and carbon tetrachloride (60 ml) was stirred at room temperature for 10 minutes and filtered to remove insoluble material (900 mg). To the filtrate was slowly added N-methylpyrrolidine (0.42 ml, 4.04 mmoles) under stirring at 0° C. The mixture was stirred at 0° C. for 1 hour, and the precipitate which formed was collected by filtration, washed with CCl$_4$ and dried to give the quaternized product (V), (2.30 g, 69%).

PMR: $\delta^{CDCl_3}$ ppm ca. 2.0 (4H, m, pyrrolidine-H), 2.78 (3H, s, N—Me$^{\oplus}$), ca. 3.3 (2H, m, H-2), ca. 3.6 (4H, m, pyrrolidine-H), 5.37 (1H, d, J=5.0 Hz, H-6), 5.75 (1H, d, H-7), 6.98 (1H, s, CHPh$_2$), ca. 7.3 and 7.7 (15H, m, Ph), ca. 8.5 (1H, br s, PhCH=N—).

Procedure I: To a solution of (V) (2.20 g, 3.24 mmoles), in 98% formic acid (22 ml) was added concentrated hydrochloric acid (1.35 ml, 16.2 mmoles), and the mixture was stirred at room temperature for 1 hour. The reaction mixture was diluted with water (50 ml), washed with ethyl acetate (2×50 ml) and concentrated under reduced pressure. To the concentrate (ca. 5 ml) was added acetone (20 ml) to give a semi-crystalline precipitate of (VI), (575 mg, 48%). Purity 85% [HPLC: $\mu$Bondapak C$_{18}$ (4×300 mm); 0.01M acetate buffer (pH4)/acetonitrile (200:5); 1 ml/minute; hereinafter System B; RT 5.5 minutes]. Mp. 165° C. (dec.). This sample showed no $\Delta^2$ isomer in HPLC and PMR spectrum. Some amount of the $\Delta^2$ isomer was observed in the acetone filtrate.

Procedure II: To a solution of (V), (10.0 g, 14.7 mmoles), in 98% formic acid (10 ml) was added concentrated hydrochloric acid (6.1 ml, 73.6 mmoles), and the mixture was stirred at room temperature for 1 hour. To the mixture was added acetone (250 ml) under vigorous stirring to give a precipitate, which was collected by filtration, washed with acetone to give a crude product of (VI) (4.4 g) as a hygroscopic solid. The crude sample was dissolved in water (20 ml) and reprecipitated by the addition of acetone (200 ml) to afford the Compound (VI) (3.08 g, 57%). Purity 85% (HPLC, System B). PMR and HPLC analysis indicated that this sample contained a small amount of the corresponding $\Delta^2$ isomer (less than 10%). [HPLC: System B, RT 5.5 minutes for (VI), 4.5 minutes for $\Delta^2$ isomer].

Recrystallization: A 210 mg sample of Procedure II was recrystallized from 1M hydrochloric acid (0.5 ml) and isopropanol (1 ml) to afford 22 mg of plates which contained no $\Delta^2$ isomer. Mp. 165° C. (dec.). Purity 90% (HPLC: System B).

IR: $\nu_{max}^{KBr}$ cm$^{-1}$ 3400, 1800, 1595.

UV: $\lambda_{max}^{pH7\ Buffer}$ nm($\epsilon$) 267 (8100).

PMR: $\delta^{D_2O}$ ppm, 2.30 (4H, m, pyrrolidine-H), 3.09 (3H, s, N—Me$^{\oplus}$), ca. 3.6 (4H, m, pyrrolidine-H), 3.62 and 4.07 (2H, ABq, J=18 Hz, H-2), 4.08 and 4.80 (2H, ABq, —CH$_2$—N$^{\oplus}$, J=14 Hz), 5.27 (1H, d, J=5 Hz, H-6) and 5.48 (1H, d, H-7).

EXAMPLE IV

Preparation of (V) From (II) Without Isolation of (III) and (IV)

A mixture of (II), (20.0 g, 48.3 mmoles), benzaldehyde (5.2 ml, 50.7 mmoles) and Na$_2$SO$_4$ (20 g) in ethyl acetate (200 ml) was stirred at room temperature for 1 hour, during which period a clear solution was obtained within 30 minutes. HPLC analysis of an aliquot of the reaction mixture showed that the starting material (II) (System A, RT 3.5 minutes) was quickly consumed.

To the mixture was added a solution of sodium iodide (8.7 g, 58 mmoles) in acetone (40 ml), and the mixture was stirred at room temperature for 30 minutes. HPLC analysis (System A) indicated the complete displacement of the chloride (III) to the iodide (IV); RT 6.0 minutes for (III), 7.0 minutes for (IV). The reaction mixture was filtered through diatomaceous earth and the filtrate was washed with saturated solutions of Na$_2$S$_2$O$_3$ and NaCl successively, dried over Na$_2$SO$_4$ and evaporated to dryness.

The resulting syrup was diluted with carbon tetrachloride (500 ml) and the insolubles were filtered off. To the cold filtrate was added slowly N-methylpyrrolidine (6.6 ml, 63.8 mmoles), and the mixture was stirred at 0° C. for 1 hour. The precipitate which formed was collected by filtration to afford Compound (V), 29.1 g, 89% yield from (II).

Compound (V) is readily converted to Compound (VI) by the Procedures I or II of Example III.

EXAMPLE V

Preparation of (V) From (III)

Method A

To a stirred solution of (III), 10 g, 20 mmoles, in toluene (200 ml) was added dropwise over a period of 15 minutes a solution of sodium iodide (2.97 g, 20 mmoles) in acetone (60 ml) under a nitrogen atmosphere. The mixture was stirred for 45 minutes at room temperature, washed consecutively with saturated solutions of Na$_2$S$_2$O$_3$ (300 ml) and NaCl (300 ml×2), and dried over anhydrous Na$_2$SO$_4$ (20 g). The solution was filtered and to the stirred filtrate was added dropwise at 0°-5° C. over a period of 50 minutes a solution of N-methylpyrrolidine (2.07 ml, 20 mmoles) in toluene (30 ml) under a nitrogen atmosphere. The mixture was stirred for an additional 10 minutes at the same temperature. n-Heptane (200 ml) was added to the reaction mixture to give a precipitate, which was collected by filtration, washed with n-heptane (50 ml) and dried over P$_2$O$_5$ to afford 11.6 g of Compound (V), which contained the $\Delta^2$ isomer ($\Delta^2/\Delta^3$=1/6, estimated by HPLC). Estimated purity 60% (by HPLC).

Method B

To a stirred solution of (III), 10 g, 20 mmoles, in ethyl acetate (150 ml) was added dropwise, over a period of 15 minutes a solution of sodium iodide (3.6 g, 24 mmoles) in acetone (30 ml) under nitrogen atmosphere. The mixture was stirred for 30 minutes at room temperature and filtered through a diatomaceous earth pad. The filtrate was evaporated in vacuo and the residue was dissolved in toluene (100 ml). The insoluble material was removed by filtration. To the chilled ($-5°$ to $-10°$ C.) and stirred filtrate was added dropwise a solution of N-methylpyrrolidine (2.07 ml, 20 mmoles) in toluene (30 ml) under nitrogen atmosphere. It required 30 minutes. The mixture was stirred for an additional 30 minutes at the same temperature and diluted with n-heptane (200 ml). The precipitate which formed was collected by filtration, washed with n-heptane and dried over $P_2O_5$ to give 12.8 g of Compound (V), which contained a small amount of the $\Delta^2$ isomer ($\Delta^2/\Delta^3 = 1/12$). Estimated purity 60%.

Compound (V) is readily converted to (VI) by the method of Example III.

EXAMPLE VI

Preparation of (VI, X=HCl) From (V)

Concentrated hydrochloric acid (25 ml, 0.30 mole, 3.0 equivalents) was added to 95–97% formic acid (68 ml, 1.7 mole, 17 equivalents) with good stirring at ambient temperature. Compound (V), (68 g, 0.10 mole), was then added to the mixture in portions over five (5) minutes with good stirring. An exotherm of ca. 5° C. may be expected. An additional amount of 95–97% formic acid (4 ml, 0.11 mole, 1.1 equivalents) was used to wash in the Compound (V) not transferred in the first additions.

The resulting dark brown slurry was stirred for an additional sixty (60) minutes at ambient temperature following the addition.

The solution was poured into 2.5 L of acetone over a period of ca. thirty (30) seconds, with good stirring. To the resulting suspension of crude (VI), a yellowish solid, in acetone was added diatomaceous earth (34 g) in one portion. The resulting suspension was stirred an additional five (5) minutes at ambient temperature.

The suspension was filtered through a buchner funnel using house vacuum suction. The filter cake was pressed down with a spatula and was subsequently washed with an additional portion of acetone (1×200 ml). The filter cake was partially dried under house vacuum suction for five (5) minutes.

The filter cake was added in portions to 250 ml of water with good stirring. After an additional five (5) minutes, the resulting suspension was filtered through a coarse sintered glass funnel. The filter cake was washed with an additional 50 ml of water.

To the filtrate was added 6.8 g of activated carbon with good stirring. The resulting suspension was stirred at ambient temperature for an additional twenty-five (25) minutes.

A total of 10 g of diatomaceous earth was added to the suspension at this point, and stirring was continued for an additional five (5) minutes.

The suspension was filtered under house vacuum suction through a coarse sintered glass funnel. The vessel was then rinsed with water (100 ml), and the rinsings were used to wash the filter pad. The filtrate obtained from this operation was typically yellowish orange in color. Volume ca. 400 ml.

Crystalline (VI) was precipitated from the aqueous solution by dropwise addition of 2.0 L of acetone with good agitation. The acetone was added slowly until the cloud point was reached (ca. 325 ml of acetone added). At this point, the addition of acetone was stopped and seed crystals were added. Once the crystallization was well underway, the remaining portion of acetone was added dropwise at an increased rate of addition.

Following the addition, the suspension of (VI) in acetone/$H_2O$ was cooled to $0°$–$5°$ C. and was stirred for thirty (30) minutes.

The suspension was filtered through a buchner funnel under house vacuum suction. The filter cake was washed with an additional amount of acetone (1×200 ml). The collected solid was partially dried under house vacuum suction for five (5) minutes.

The snow white filter cake of (VI) which resembled a piece of filter paper in appearance was broken up into small chunks and was dried for 16 hours at 0.05 mm Hg (vacuum pump) at ambient temperature.

A total of 16.2 g (49%) of (VI) was obtained as a snow white hygroscopic, crystalline and electrostatic solid.

EXAMPLE VII

Conversion of (VI, X=HCl) to (VII)

A sample of (VI, X=HCl), (21.72 g, 0.0612 mole), was dissolved in water (190 ml) at 25° C. with stirring. The mixture was then cooled to 8°–10° C. and the pH adjusted from 2.5 to 5.8 (range 5.7–5.9) by the dropwise addition of sodium hydroxide solution (2N, 30.5 ml, 0.061 mole, 1.0 equivalent). Total volume was 214 ml.

Tetrahydrofuran (THF, 555 ml) was then added in three portions. The temperature of the mixture after each addition rose to 12°–13° C. and was allowed to return to 8°–10° C. before the next portion was added. The total addition time was 10 minutes. The pH of the mixture was 5.8–6.1.

The pH of the mixture was then adjusted to 6.8 (range 6.7–6.9) by the dropwise addition of sodium hydroxide solution (2N, 2.0 ml, 0.004 mole).

A sample of the active ester previously described (29.5 g, 0.0927 mole) was added to the reaction mixture in five equal portions over 45 minutes. The cooling bath was removed after the first portion of the active ester had been added. The pH of the reaction mixture was readjusted to 6.5 (range 6.5–6.7) 5–10 minutes after each addition of the active ester by the dropwise addition of sodium hydroxide solution (2N).

The clear, pale orange reaction mixture was stirred for 2–3 hours at 25° C. In the initial 30 minutes, the pH was readjusted to 6.5 (range 6.5–6.7) every 5–10 minutes by the dropwise addition of 2N sodium hydroxide solution. In the remaining reaction time, the pH was readjusted to 6.5 every 15 minutes (total 2N NaOH: 29.5 ml, 0.059 mole, 0.97 equivalent). The completion of the reaction was judged by HPLC analysis.

Solids present in the reaction mixture were then removed by filtration and washed with water (2×5 ml). The filtrate was extracted with methyl isobutyl ketone (MIBK, 790 ml) and the aqueous layer separated. The organic phase was washed with water (64 ml), and the aqueous phases combined and stirred with Dicalite (5.1 g) for 10 minutes. The solids were removed by suction filtration and washed with water (2×5 ml).

The resulting clear orange solution (volume 314 ml) was acidified with good stirring to pH 3.7 (range 3.5–4.0) by the dropwise addition of sulfuric acid (4N, 14.5 ml). At this point the mixture became cloudy and crystallization of the sulfuric acid addition salt of (VII) began.

The crystallization was allowed to proceed for 10–15 minutes, and then the pH was adjusted to 3.0 (range 2.9–3.1) by the dropwise addition of sulfuric acid (4N, 7.5 ml). The mixture was cooled to 0° to 5° C. and the remaining sulfuric acid (4N, 63.5 ml) was added over 20–30 minutes (resulting pH: 1.3–1.5). After the addition of sulfuric acid was complete, the slurry was stirred for 1 hour at 0° to 5° C.

The white crystalline product was removed by suction filtration and washed with sulfuric acid (0.5N, 63.5 ml). The solids were partially dried under suction for 15 minutes and then washed with acetone (2×100 ml). The solids were again partially dried under suction for 10 minutes and then slurried for 1 hour in acetone (400 ml) with good agitation. The solids were removed by suction filtration, washed with acetone (2×100 ml) and dried in vacuo (10–15 mm Hg) at 35°–40° C. to constant weight (3–6 hours).

The product, the sulfuric acid addition salt of (VII), was recovered as a slightly electrostatic, white crystalline solid (28.79 g, 81.4%).

EXAMPLE VIII

Conversion of (VI, $X=H_2SO_4$) to (VII)

The general procedure of Example VII is repeated except that the (VI, X=HCl) starting material is replaced by an equimolar amount of (VI, $X=H_2SO_4$), and the title compound is thereby produced.

Other variations will be evident to those skilled in the art. Therefore, the scope of the invention is intended to be defined by the claims.

We claim:

1. Temperature stable crystalline salts of 7-amino-3-(1-methylpyrrolidinio)methyl-3-cephem-4-carboxylate substantially free of $\Delta^2$ isomer, selected from the group consisting of the mono-hydrochloric and sulfuric acid addition salts.

2. The salt of claim 1 which is the mono-hydrochloric acid addition salt.

3. The salt of claim 1 which is the sulfuric acid addition salt.

* * * * *